US012758713B2

(12) United States Patent
Boström

(10) Patent No.: US 12,758,713 B2
(45) Date of Patent: Oct. 13, 2026

(54) POWERPACK SUB-ASSEMBLY

(71) Applicant: SHL MEDICAL AG, Zug (CH)

(72) Inventor: Anders Boström, Ingarö (SE)

(73) Assignee: SHL Medical AG, Zug (CH)

( * ) Notice: Subject to any disclaimer, the term of this patent is extended or adjusted under 35 U.S.C. 154(b) by 652 days.

(21) Appl. No.: 18/277,541

(22) PCT Filed: Dec. 10, 2021

(86) PCT No.: PCT/EP2021/085126

§ 371 (c)(1),
(2) Date: Aug. 16, 2023

(87) PCT Pub. No.: WO2022/184304

PCT Pub. Date: Sep. 9, 2022

(65) Prior Publication Data

US 2024/0123149 A1 Apr. 18, 2024

(30) Foreign Application Priority Data

Mar. 1, 2021 (EP) .................................... 21160051

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31571* (2013.01); *A61M 5/3243* (2013.01)

(58) Field of Classification Search
CPC ................ A61M 5/50; A61M 5/31501; A61M 2005/3247
See application file for complete search history.

(56) References Cited

U.S. PATENT DOCUMENTS 6,805,686 B1 10/2004 Fathallah et al.
7,717,877 B2 5/2010 Lavi et al.
(Continued)

FOREIGN PATENT DOCUMENTS

CN 109922848 A 6/2019
EP 1654020 B1 3/2010
(Continued)

OTHER PUBLICATIONS

International Search Report and Written Opinion for Int. App. No. PCT/EP2021/085126, mailed Mar. 18, 2022.

*Primary Examiner* — Courtney Fredrickson
(74) *Attorney, Agent, or Firm* — McDonnell Boehnen Hulbert & Berghoff LLP

(57) ABSTRACT

A powerpack sub-assembly for a medicament delivery device is described, the powerpack sub-assembly extending along an axis in an axial direction from a proximal end to a distal end. The powerpack sub-assembly has a housing extending from the distal end of the powerpack sub-assembly, a lock ring slidable in the axial direction relative to the housing, an activation ring slidable in the axial direction relative to the housing and relative to the lock ring, wherein the lock ring is arranged closer to the distal end of the powerpack sub-assembly than the activation ring, a connection mechanism to connect the activation ring to the lock ring during use, the connection mechanism has a connector on the activation ring and a corresponding connector on the lock ring, and a lock mechanism to lock the powerpack sub-assembly after use, the lock mechanism having a distally-facing surface on the lock ring and a corresponding proximally-facing surface on the housing.

20 Claims, 6 Drawing Sheets

(56) References Cited

U.S. PATENT DOCUMENTS

| | | | | |
|---|---|---|---|---|
| 10,493,212 | B2 | 12/2019 | Tschirren et al. | |
| 2012/0226233 | A1* | 9/2012 | Schraga .............. | A61M 5/3205 604/111 |
| 2014/0371670 | A1 | 12/2014 | Holmqvist et al. | |
| 2017/0080159 | A1 | 3/2017 | Wei | |
| 2019/0381251 | A1 | 12/2019 | Mosebach et al. | |
| 2020/0164138 | A1 | 5/2020 | Holmqvist | |
| 2020/0297930 | A1 | 9/2020 | Hommann et al. | |

FOREIGN PATENT DOCUMENTS

| | | | |
|---|---|---|---|
| EP | 2632518 | B1 | 6/2016 |
| EP | 2060292 | B1 | 7/2016 |
| EP | 3305348 | A2 | 4/2018 |
| EP | 3104909 | B1 | 10/2019 |
| EP | 3651838 | B1 | 3/2021 |
| WO | 2007/131013 | A1 | 11/2007 |
| WO | 2009/003300 | A1 | 1/2009 |
| WO | 2009/040607 | A1 | 4/2009 |
| WO | 2010/108116 | A1 | 9/2010 |
| WO | 2011123024 | A | 10/2011 |
| WO | 2012/022810 | A2 | 2/2012 |
| WO | 2012105898 | A1 | 8/2012 |
| WO | 2012/122643 | A1 | 9/2012 |
| WO | 2015/121080 | A1 | 8/2015 |
| WO | 2016/015165 | A1 | 2/2016 |
| WO | 2018206583 | A | 11/2018 |
| WO | 2019/011689 | A1 | 1/2019 |
| WO | 2019/121024 | A1 | 6/2019 |
| WO | 2020/074570 | A1 | 4/2020 |

* cited by examiner

POWERPACK SUB-ASSEMBLY

CROSS REFERENCE TO RELATED APPLICATIONS

The present application is a U.S. National Phase Application pursuant to 35 U.S.C. § 371 of International Application No. PCT/EP2021/085126 filed Dec. 10, 2021, which claims priority to European Patent Application No. 21160051.5 filed Mar. 1, 2021. The entire disclosure contents of these applications are herewith incorporated by reference into the present application.

TECHNICAL FIELD

The present disclosure concerns powerpack sub-assemblies, and particularly powerpack sub-assemblies with a lock mechanism.

BACKGROUND

Medicament delivery devices such as autoinjectors can include a lock mechanism to avoid premature medicament delivery. The applicant has appreciated that improvements can be made compared to these existing lock mechanisms.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

One aspect of the present disclosure concerns a powerpack sub-assembly for a medicament delivery device, the powerpack sub-assembly extending along an axis in an axial direction from a proximal end to a distal end, the powerpack sub-assembly comprising a housing extending from the distal end of the powerpack sub-assembly, a lock ring slidable in the axial direction relative to the housing, an activation ring slidable in the axial direction relative to the housing and relative to the lock ring, wherein the lock ring is arranged closer to the distal end of the powerpack sub-assembly than the activation ring, a connection mechanism to connect the activation ring to the lock ring during use, the connection mechanism comprising a connector on the activation ring and a corresponding connector on the lock ring, and a lock mechanism to lock the powerpack sub-assembly after use, the lock mechanism comprising a distally-facing surface on the lock ring and a corresponding proximally-facing surface on the housing. This can provide a powerpack sub-assembly which can have a clear activation point, with the activation provided by axial movement of the activation ring. This can provide a powerpack sub-assembly which includes a lock which can stop reuse of a used device.

Optionally, the powerpack sub-assembly comprises a spring arranged between the housing and the activation ring. Optionally, the housing comprises a flexible arm extending in the proximal direction, wherein the proximally-facing surface on the housing is on the arm. Optionally, the flexible arm is flexible in a radial direction relative to the axis. Optionally, the housing, the activation ring and the lock ring are all coaxial. Optionally, the housing comprises a tubular portion, and the activation ring and the lock ring both extend around the tubular portion of the housing.

Optionally, the connection mechanism is a snap-fit. Optionally, the connector on the lock ring is a hook on a flexible arm. Optionally, the connector on the activation ring is a protrusion or rib. Optionally, the flexible arm is flexible in a circumferential direction relative to the axis.

Optionally, the housing and the lock ring are rotationally locked relative to one another. Optionally, the housing and the activation ring are rotationally locked relative to one another. The provision of rotational locks between the housing on one hand and the lock ring and activation ring on the other hand can help ensure that the connection mechanism is aligned.

During use, the activation ring can be moveable in a distal direction from a position spaced apart from the lock ring to a position adjacent to the lock ring, and the activation ring and the lock ring can subsequently be moveable together relative to the housing from a distal position to a proximal position, so as to lock the powerpack sub-assembly after use. Optionally, the connection mechanism connects the activation ring to the lock ring when the activation ring moves to the position adjacent to the lock ring.

Optionally, the powerpack sub-assembly comprises a plunger rod and the housing comprises a flexible arm, wherein at least part of the flexible arm is inside the activation ring, and wherein a portion of the flexible arm of the housing extends into a recess in the plunger rod. When the activation ring moves in the distal direction, the flexible arm is no longer restricted from flexing away from the axis by the activation ring, which can allow the flexible arm to move out of the recess in the plunger rod, thereby allowing the plunger rod to move in the axial direction and activating a medicament delivery device of which the powerpack sub-assembly is of part.

Another aspect of the present disclosure comprises an autoinjector comprising the powerpack sub-assembly of any previous claim. Optionally, the autoinjector comprises a needle shield that abuts the activation ring.

Another aspect of the present disclosure comprises a powerpack sub-assembly comprising a housing, a lock ring and an activation ring, wherein when the activation ring is moved in the distal direction, the lock ring is connected to the activation ring, and wherein when the activation ring is subsequently moved in the proximal direction, the activation ring and the lock ring move together in the proximal direction.

Another aspect of the present disclosure comprises a powerpack sub-assembly comprising a housing, a lock ring and an activation ring, wherein in a first state, the activation ring is in a first proximal position and the lock ring is in a distal position relative to the housing, wherein the activation ring is spaced apart from the lock ring in the axial direction, wherein in a subsequent second state, the activation ring is in a distal position and the lock ring is in the distal position and the activation ring is adjacent to the lock ring, and wherein in a subsequent third state, the activation ring is in a second proximal position (which is optionally the same as the first proximal position) and the lock ring is in a proximal position, wherein the activation ring is adjacent to the lock ring.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

BRIEF DESCRIPTION OF THE DRAWINGS

Embodiments of the present disclosure will now be described by way of example only and with reference to the accompanying drawings, in which.

DETAILED DESCRIPTION

Figure 1:
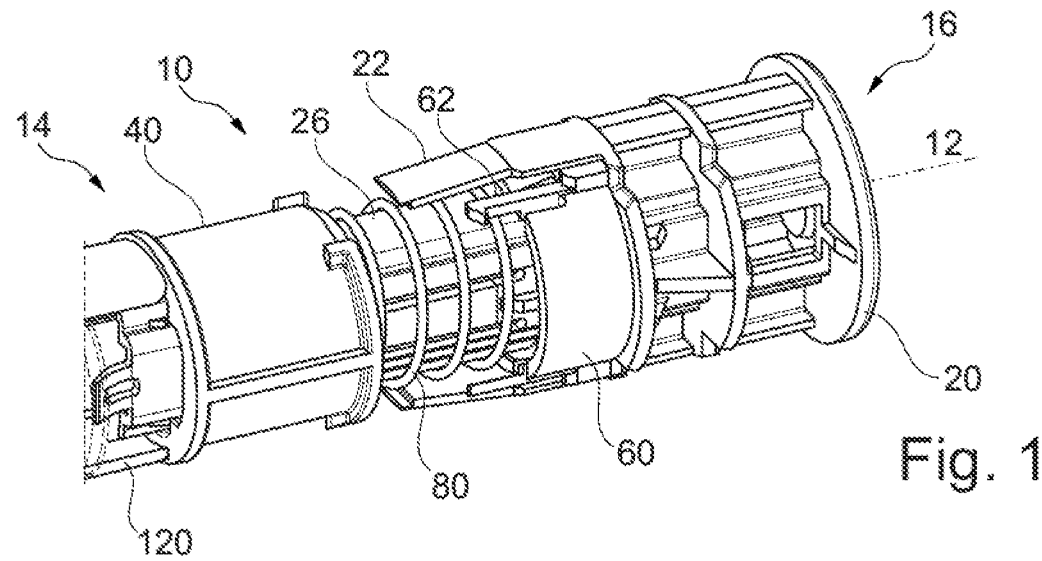
FIG. 1 shows a perspective view of a powerpack sub-assembly with a needle shield for context.

A powerpack sub-assembly 10 will now be described. The powerpack sub-assembly 10 (see for example FIG. 1) extends in an axial direction along an axis 12 from a proximal end 14 to a distal end 16. The powerpack sub-assembly 10 comprises a housing 20 (or rear housing), an activation ring 40, a lock ring 60 and an optional spring 80. The housing 20 extends from the distal end 16 of the powerpack sub-assembly 10. The lock ring 60 is slidable in the axial direction relative to the housing. The activation ring 40 is slidable in the axial direction relative to the housing and slidable relative to the lock ring 60. The lock ring 60 is arranged closer to the distal end 16 of the powerpack sub-assembly 10 than the activation ring 40.

The powerpack sub-assembly 10 comprises a connection mechanism. The connection mechanism can connect the lock ring to the activation ring during use. The connection mechanism comprises a connector on the lock ring and a corresponding connector on the activation ring. In this example, the connector on the activation ring 40 is a protrusion 46, and the connector on the lock ring is a hook 64 on a flexible arm 62 (see for example FIG. 4). Alternatively, the connector on the lock ring could be a protrusion, and the connector on the activation ring a hook on a flexible arm. Other snap-fit designs could alternatively be used, or other types of connections, such as a friction-fit connection.

The powerpack sub-assembly 10 also comprises a lock mechanism. The lock mechanism can lock the powerpack sub-assembly 10 after use. The lock mechanism comprises a distally-facing surface on the lock ring and a corresponding proximally-facing surface on the housing. In this example, the distally-facing surface on the lock ring is a distally-facing surface 72 of a protrusion 70, and the proximally-facing surface on the housing is a proximally-facing surface 24 on a flexible arm 22 of the housing 20 (see FIG. 6).

Figure 11:
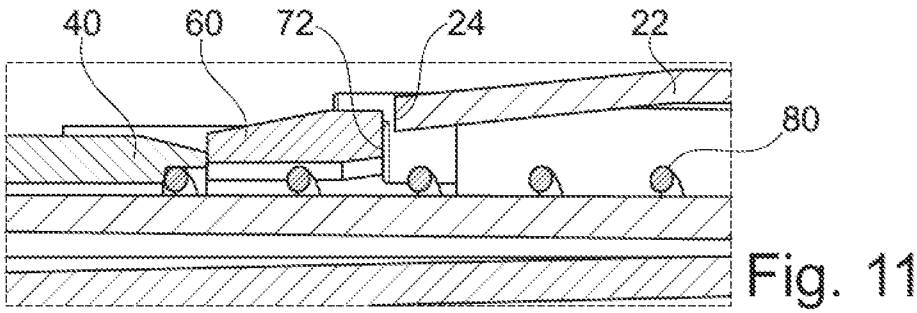
FIG. 11 shows a cross-section view of an alternative approach for the interacting surfaces on the lock ring and the housing.
Figure 12:
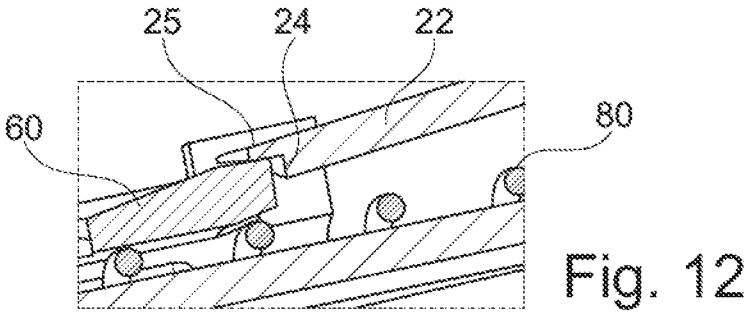
FIGS. 12 and 13 show the interacting surfaces on the lock ring and the housing of the powerpack sub-assembly of FIG. 1.
Figure 13:
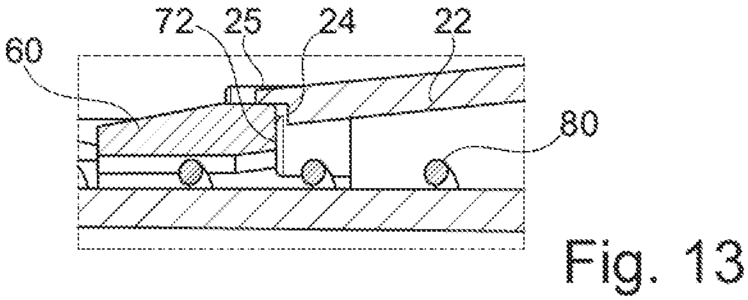

FIGS. 11 to 15 show three examples of how the lock ring and the housing could interact. FIGS. 12 and 13 show a close-up of the approach used in the example above, for example in FIGS. 6 and 9. In this approach, in addition to the proximally-facing surface 24 and the distally-facing surface 72, there is a proximally-extending protrusion 25 at the proximal end of the flexible arm 22. The proximally-extending protrusion 25 extends further in the proximal direction than the proximally-facing surface 24 of the flexible arm 22, and can therefore provide radial support for the alignment of the proximally-facing surface 24 and the distally-facing surface 72. The proximally-extending protrusion 25 is preferably further from the axis 12 (see FIG. 1) than the distally-facing surface 72.

Figure 14:
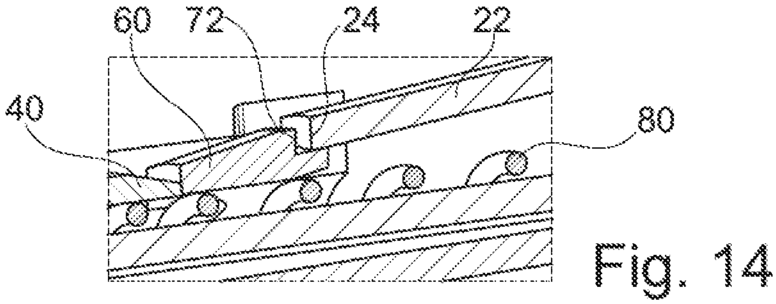
FIGS. 14 and 15 show another alternative shape for the interacting surfaces on the lock ring and the housing.
Figure 15:
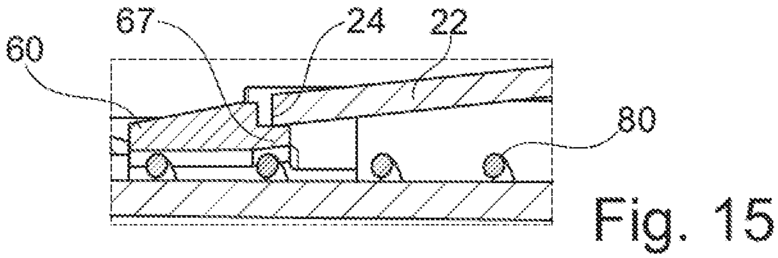

FIGS. 14 and 15 show an approach in which a distally-extending protrusion 67 is provided at the distal end of the lock ring 60. The distally-extending protrusion 67 extends further in the distal direction than the distally-facing surface 72, and can therefore provide radial support for the alignment of the proximally-facing surface 24 and the distally-facing surface 72. The distally-extending protrusion 25 is preferably closer to the axis 12 (see FIG. 1) than the proximally-facing surface 24.

FIG. 11 shows an alternative approach in which no axially-extending protrusion 25 is provided. In another alternative, both the proximally-extending protrusion 25 of FIG. 12 and the distally-extending protrusion 67 are provided.

Figure 2:
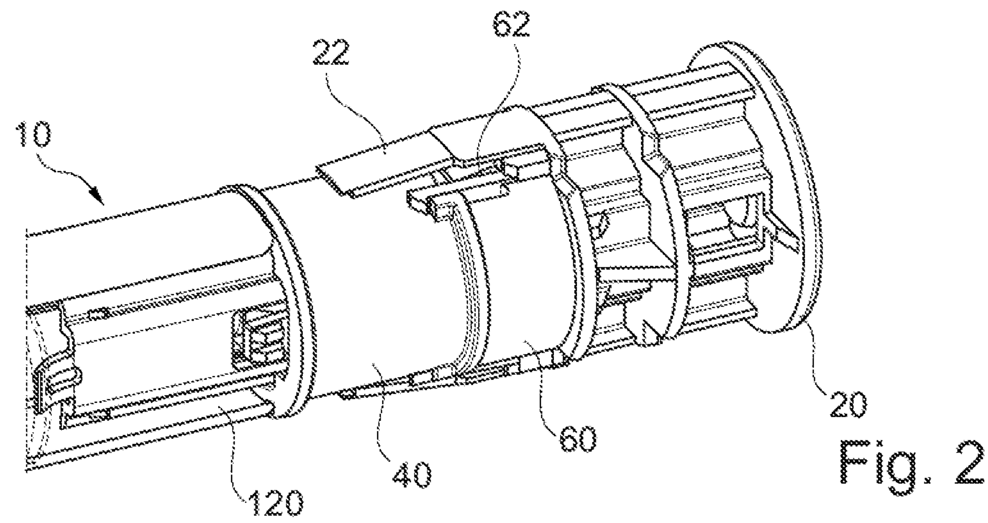
FIG. 2 shows the components of FIG. 1 during medicament delivery.
Figure 3:
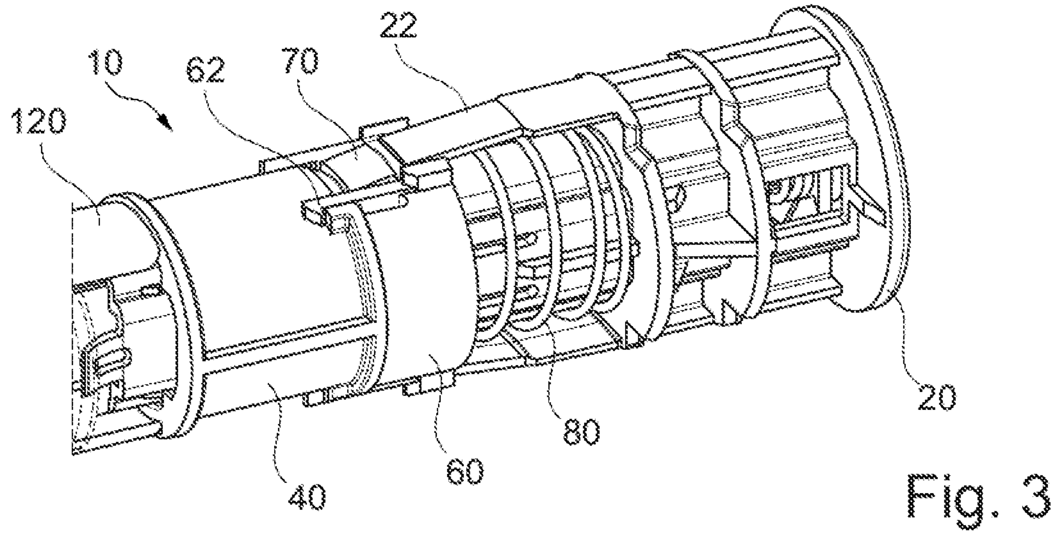
FIG. 3 shows the components of FIG. 1 after medicament delivery.

The method of operation of the powerpack sub-assembly 10 will now be described with reference to FIGS. 1 to 3. Prior to use, the powerpack sub-assembly 10 would typically be in the configuration shown in FIG. 1. In this configuration, the lock ring 60 is in a first position (distal position) relative to the housing 20 and the activation ring 40 is in a first position (first proximal position) relative to the housing 20. The activation ring 40 is spaced apart from the lock ring 60.

During use of a medicament delivery device containing a powerpack sub-assembly as described herein, the activation ring 40 is first pushed in the distal direction relative to the housing 20. The activation ring 40 thereby moves from the first position to a second position (distal position). Typically, the lock ring 60 does not move at this stage. In the illustrated example, the activation ring 40 is pushed in the distal direction by a needle shield 120, although another activator (such as a button) could alternatively push the activation ring 40 in the distal direction. After the activation ring 40 is pushed in the distal direction, the lock ring 60 is attached to the activation ring 40 by the connection mechanism. In this example, the injection would proceed with the powerpack sub-assembly 10 in the position shown in FIG. 2 (see also FIG. 9—in this example, since the second flexible arm 32 of the housing 20 is now able to move away from the axis as the activation ring 40 no longer blocks movement of the second flexible arm 32 of the housing 20, which allows the plunger rod 108 to move in the proximal direction and start delivery of a medicament when provided within a medicament delivery device). At this stage, the activation ring 40 is adjacent to the lock ring 60 as shown in FIG. 2, although there could also still be a gap between the lock ring 60 and the activation ring 40.

Once the injection has been completed (or in this example also if the user prematurely removes the medicament delivery device from the injection site during injection), the needle shield 120 moves in the proximal direction. In this example, the spring 80 then pushes the activation ring 40 from the second position to a third position (second proximal position). In this case, the third position is the same as the first position, though the third position could also be a different position to the first position. As the lock ring 60 is now attached to the activation ring 40 by the connection mechanism, the lock ring 60 also moves with the activation ring 40 (from the first position of the lock ring 60 to a second position (proximal position)). In this final position, the lock mechanism is activated—the distally-facing surface on the lock ring (in this case on the protrusion 70 of the lock ring 60) and a corresponding proximally-facing surface on the housing (in this case on the flexible arm 22) oppose each other to stop the lock ring 60 from moving back to its original position (first position), even if the needle shield 120 is pushed in the distal direction.

The structure of the components shown above will now be described in more detail with reference to FIGS. 4 to 6, which show the lock ring 60, the activation ring 40 and the housing 20 respectively.

Figure 4:
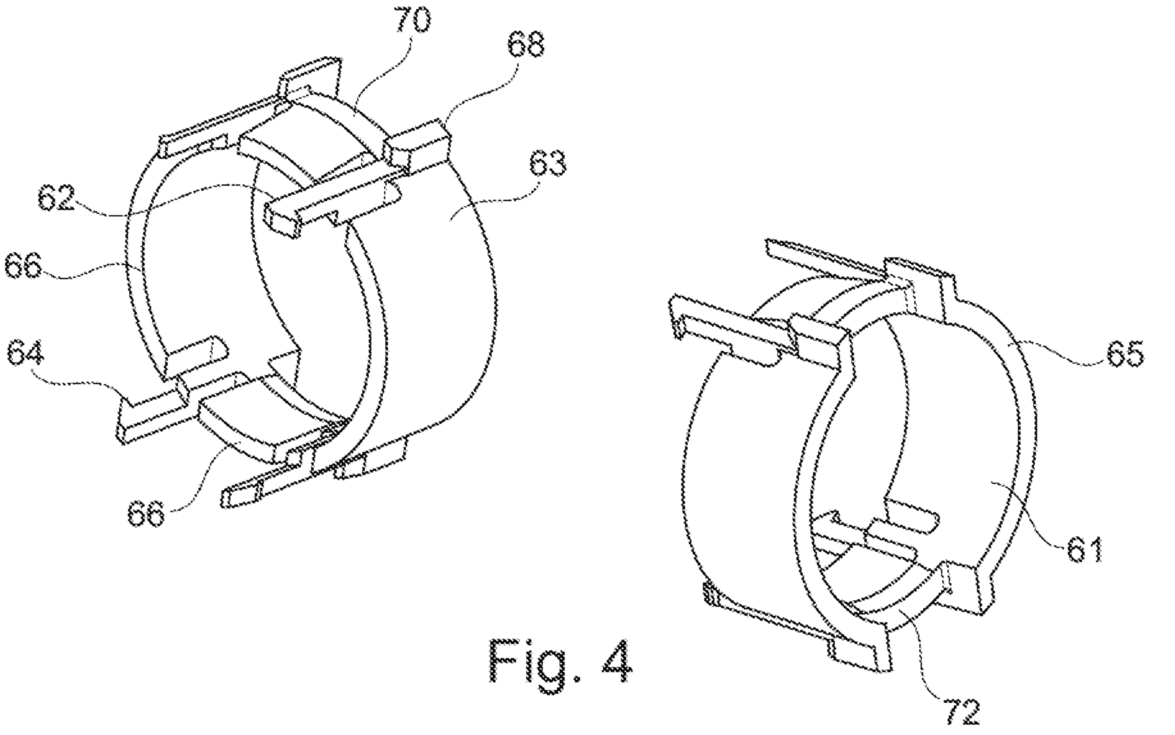
FIG. 4 shows two perspective views of the lock ring of FIG. 1.

In FIG. 4, two views of the lock ring 60 are shown. The lock ring comprises an inside surface 61 and an outside surface 63. Various features can be seen on the ring structure, including flexible arms 62 with hooks 64, support surfaces 66 and protrusions 70 of the lock ring 60, the protrusions each comprising a distally-facing surface 72. Optional ribs 68 are also shown. In this example, the distally-facing surface 72 is distinct from the distal end surface 65 of the lock ring 60, with the distally-facing surface 72 set back from the distal end surface 65 in the axial direction, but the distally-facing surface could alternatively be a part of the distal end surface.

Figure 5:
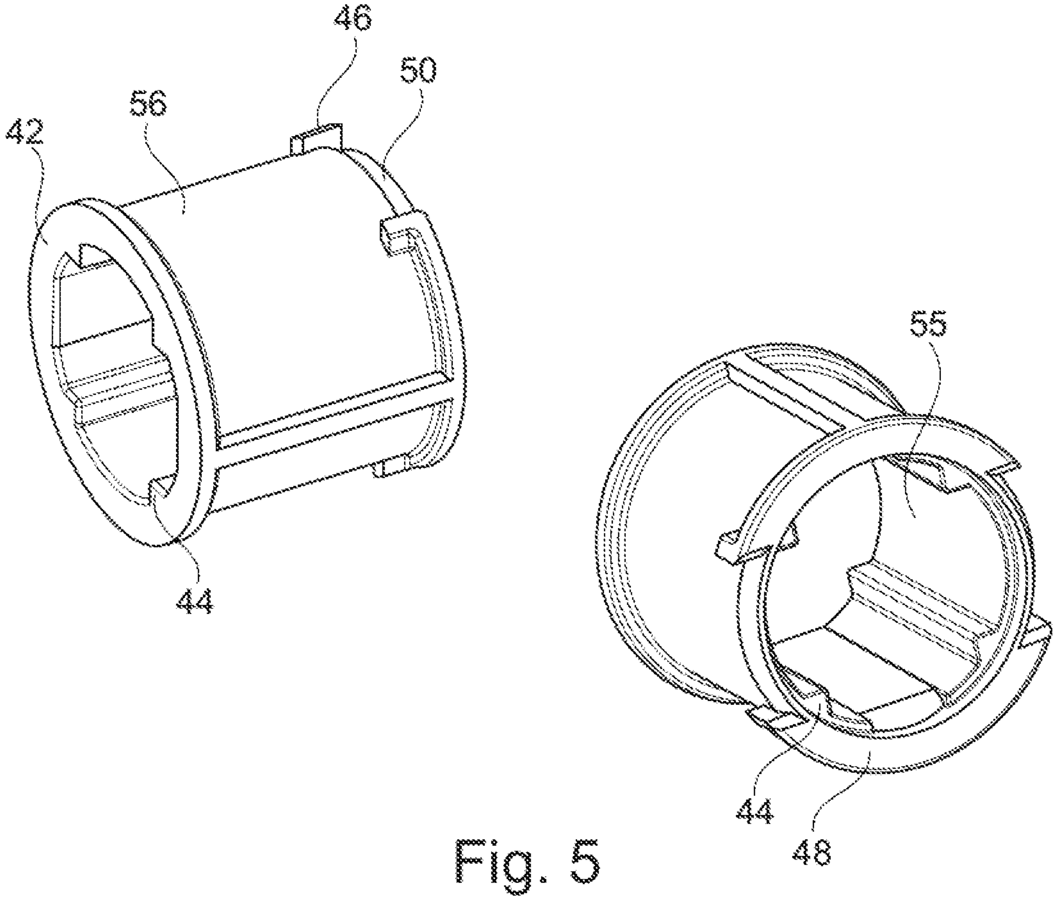
FIG. 5 shows two perspective views of the activation ring of FIG. 1.

In FIG. 5, two views of the activation ring 40 are shown. The activation ring comprises an inside surface 55 facing towards the axis 12 and an outside surface 56 facing away from the axis 12. Various features can be seen on the ring structure, including a proximally-facing surface 42, optional ribs 44 on the inside surface 55 of the activation ring 40, a protrusion (or rib) 46 on the outside surface 56 of the activation ring 40, a distally-facing surface 48 and an angled surface 50. The angled surface 50 is angled relative to the axis, for example at an angle between 15 and 75 degrees (preferably between 30 and 60 degrees), and is optional, but can beneficially reduce friction during use by making it easier for the activation ring 40 to move past the flexible arm 22 of the housing 20 during use.

Figure 6:
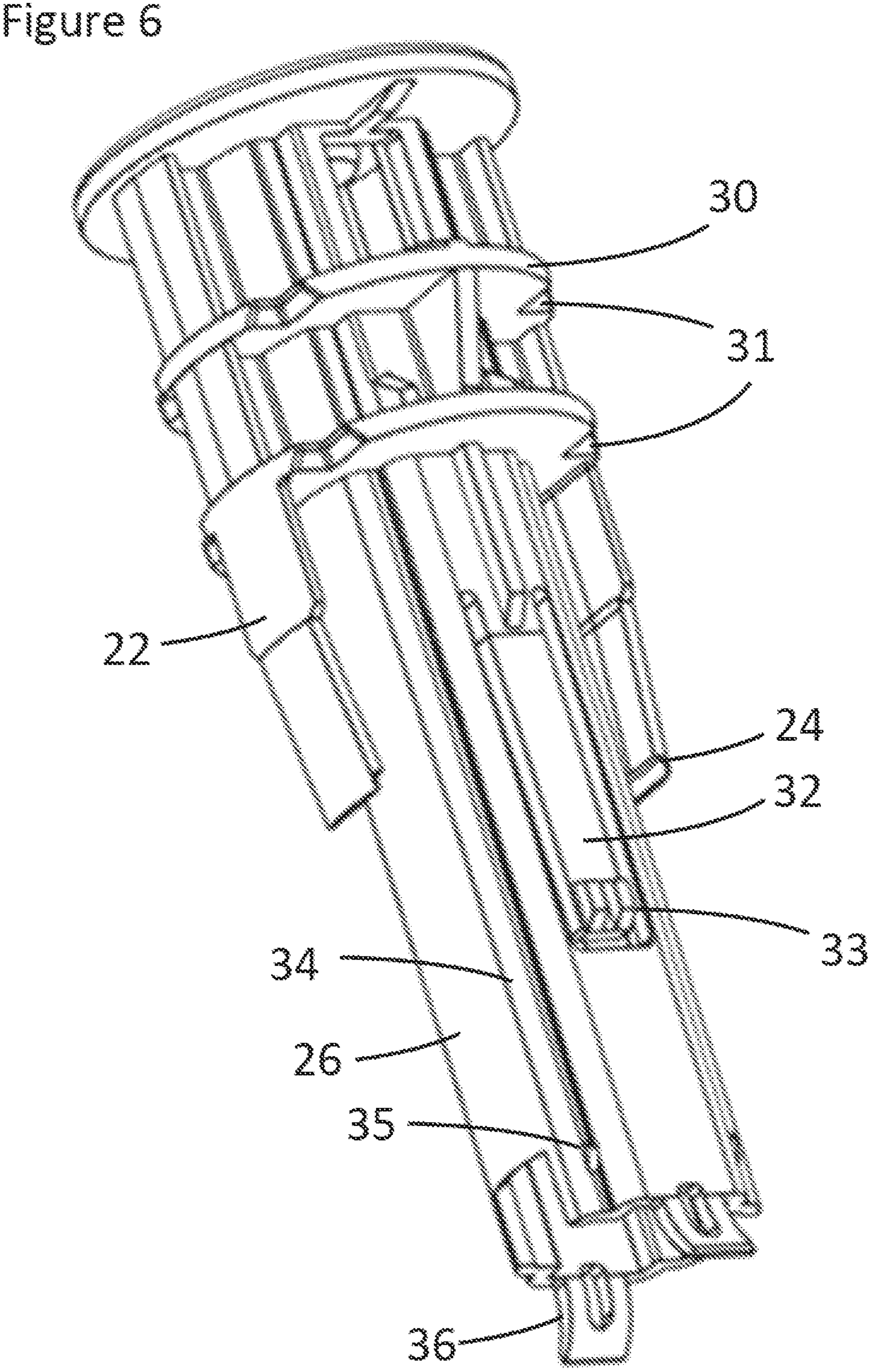
FIG. 6 shows a perspective view of the housing of FIG. 1.

In FIG. 6, the housing 20 is shown in more detail. A number of features are visible on the housing 20, including a tubular body 26 and flexible arms 22, each flexible arm having a proximally-facing surface 24. Several other optional features of the housing are also shown and will now be briefly described, including a rib 30 that can be used to help attach the housing 20 to another part of a completed medicament delivery device such as an outer housing 102, cut-outs 31 in the ribs 30 that can help with part alignment during assembly, a second flexible arm 32 that can be used for holding a plunger rod 108 in place prior to device activation, a protrusion 33 on the second flexible arm 32 that can be provided to stop device activation before the activation ring 40 has been moved in the distal direction, a longitudinal groove 34 that can interact with the rib 44 of the activation ring 40 to restrict rotation of the housing 20 relative to the activation ring 40, and a protrusion 35 in the longitudinal groove 34 that can stop the activation ring 40 from coming off the proximal end of the housing 20. An optional support arm 36 of the housing is also shown, which may be flexible and which can help support the distal end of a primary package 114 and/or can help with managing tolerances within a medicament delivery device.

Figure 7:
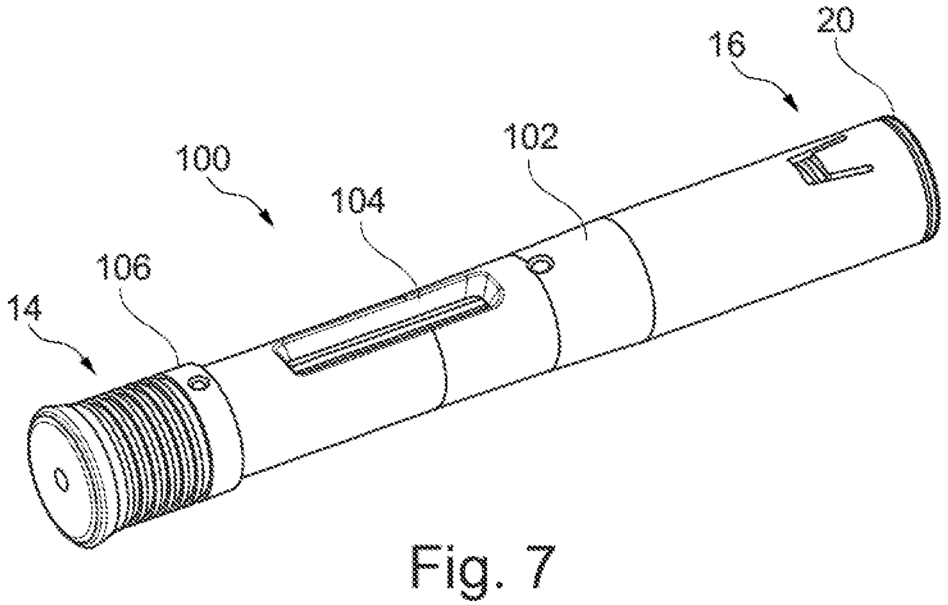
FIG. 7 shows a perspective view of an autoinjector comprising the components of FIG. 1.

The powerpack sub-assemblies described herein can be used in medicament delivery devices such as autoinjectors. One example of an autoinjector 100 in which the powerpack sub-assemblies described herein could be used is shown in FIG. 7. In FIG. 7, the housing 20 in the autoinjector 100 can be seen at the distal end 16, with a cap 106 at the proximal end 14 and an outer housing 102 (which may be a single piece or multiple pieces) extending between the cap and the housing. An optional window 104 in the outer housing 102 is also visible. Another example of an autoinjector in which the powerpack sub-assemblies described herein could be used is shown in WO2011/123024, which is hereby incorporated by reference.

An autoinjector comprising a powerpack sub-assembly as described herein would typically comprise a needle shield, an optional cap, an outer housing, a primary package containing a medicament, a syringe holder to support the primary package, and a medicament delivery member such as a needle or a jet injector. In addition, the powerpack sub-assembly would typically comprise a plunger rod as well as the powerpack sub-assembly described above. Many different designs could work with the powerpack sub-assembly described herein though. For example, the syringe holder 116 could be an integral part of the outer housing, the outer housing could be an integral part of the housing, and/or the medicament delivery member could be an integral part of the primary package, just to list a couple of simple variations.

Figure 8:
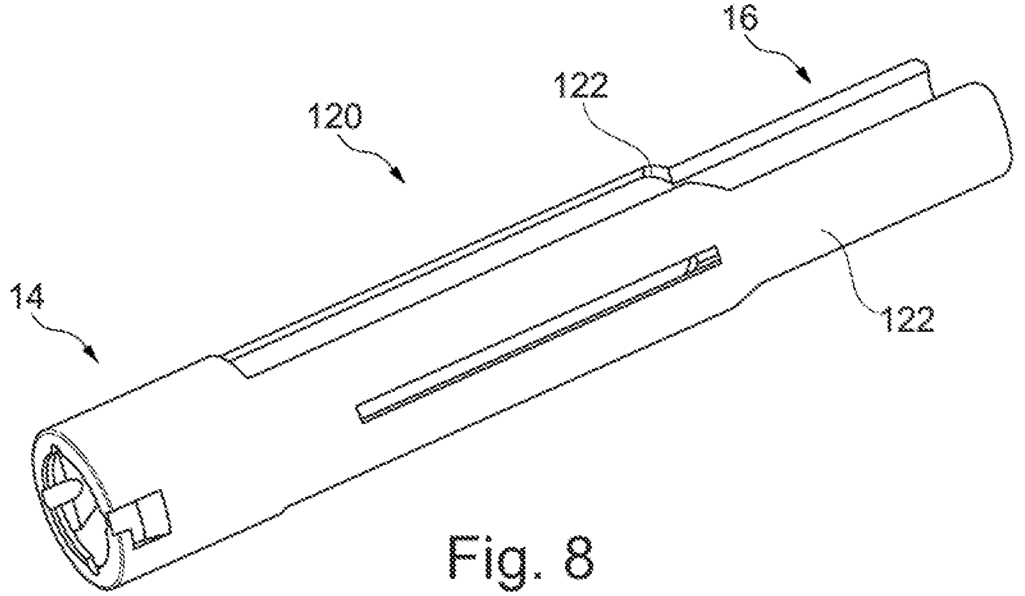
FIG. 8 shows a perspective view of the needle shield of FIG. 1.

For completeness, FIG. 8 shows an example of a needle shield 120 that could be used along with a powerpack sub-assembly as described herein. The needle shield 120 comprises two distally extending arms 122. Distally-facing surfaces of the arms can interact with the activation ring 40 as shown in FIGS. 1 to 3. The notches visible at the proximal end of the needle shield 120 are optional, but could be included to interact with a cap, for example as described in PCT/EP2020/086279, which is hereby incorporated by reference.

Figure 9:
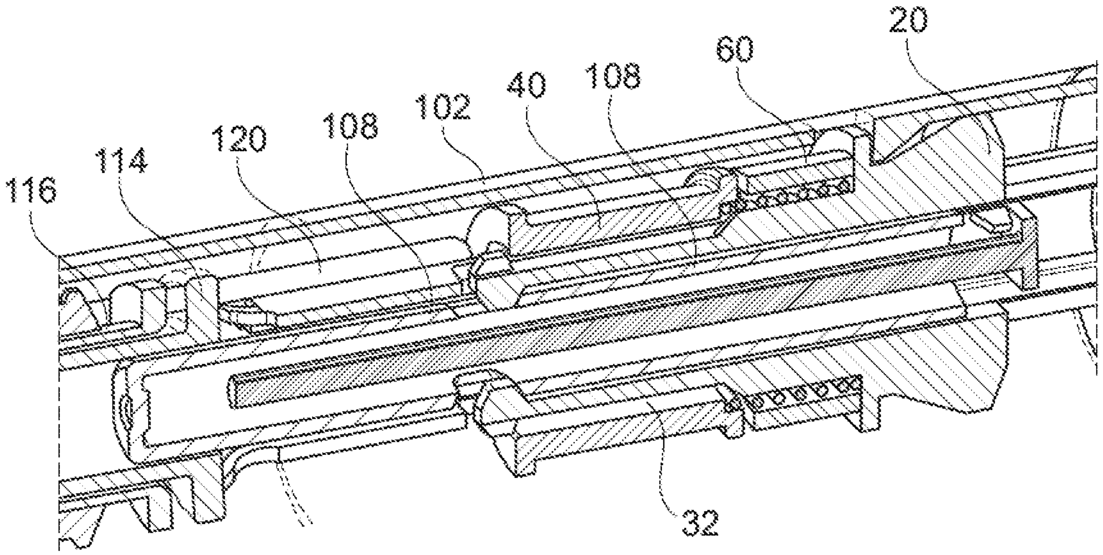
FIG. 9 shows a cross-sectional perspective view of part of the autoinjector of FIG. 7.
Figure 10:
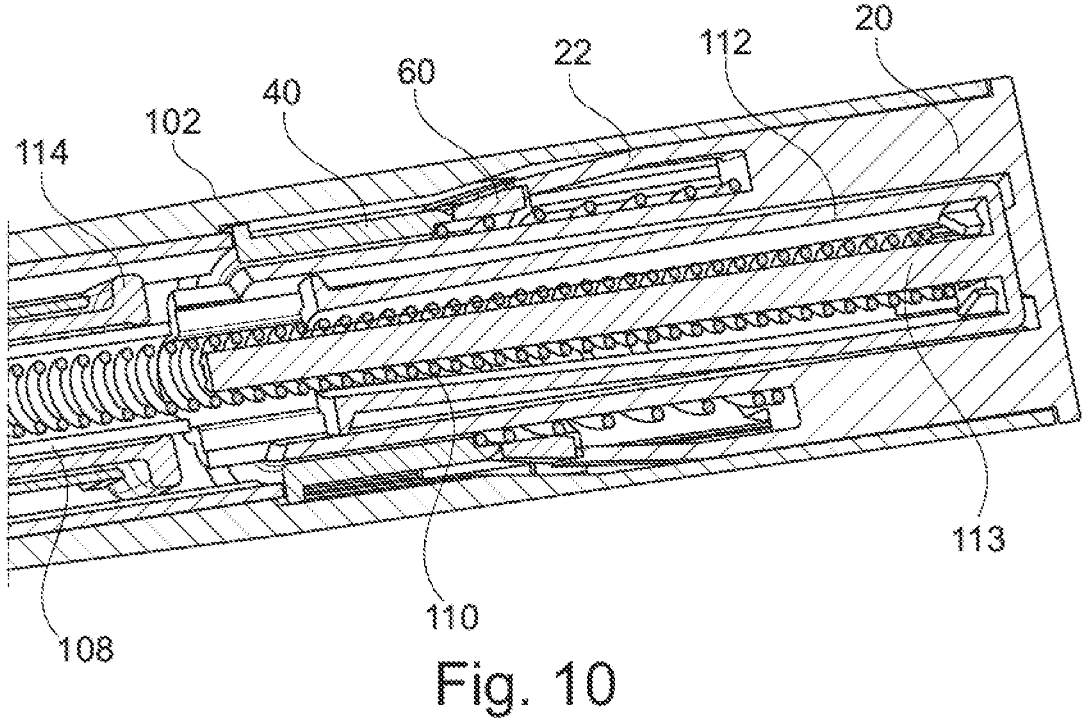
FIG. 10 shows another cross-sectional perspective view of part of the autoinjector of FIG. 7.

For context, FIGS. 9 and 10 show the powerpack sub-assembly as described with reference to FIGS. 1 to 6 inside an autoinjector. FIG. 9 shows selected components when the powerpack sub-assembly 10 is in the position shown in FIG. 2 (but without showing the plunger rod spring). FIG. 10 shows selected components when the powerpack sub-assembly 10 is in the position shown in FIG. 3. In addition to the features shown previously, a plunger rod 108, a plunger rod spring 110 and a U-bracket 112 are visible in FIG. 10 in particular.

In this example, the housing 20 (particularly the tubular portion 26 of the housing) extends through the lock ring 60 and the activation ring 40 (see e.g. FIG. 1), with the result that the housing can support the lock ring and the activation ring and keep them in place relative to the housing. This functionality could alternatively be achieved by another part of a powerpack sub-assembly or the medicament delivery device. As mentioned above, many of the structural features of the housing 20 are not essential, and will not be described in further detail.

The flexible arm 22 on the housing 20 is optional, and the proximally-facing surface on the housing could be elsewhere on the housing. The distally-facing surface on the lock ring could optionally be on a flexible arm of the lock ring. The flexible arm 22 is flexible in the radial direction, but could alternatively flex in other directions such as the circumferential direction.

Various features described herein, for example features of the lock ring 60 and the activation ring 40 as shown in FIGS. 4 and 5, are mostly provided in duplicate (and some features, such as the flexible arms 62 and ribs 68, are provided in quadruplicate). Alternatively other numbers of these features could be provided—in general, one of each feature described herein is sufficient, but providing two or more equally spaced out around the circumference can be beneficial in terms of component balance, for example in terms of force transfer between components.

The lock ring 60 and the activation ring 40 are shown as extending all the way around the axis, but one or both could alternatively extend only part way round the axis. The lock ring 60 and the activation ring 40 are each shown as circular in cross-section when viewed perpendicular to the axis, but one or both of their cross-sections could alternatively be another shape.

An optional rotational lock between the housing and the activation ring is provided in the above example by ribs 44 and corresponding longitudinal grooves 34. The rotational lock can also comprise protrusions 35, which can stop the activation ring 40 from coming off the proximal end of the housing 20. The rotational lock could also be provided in other ways, for example by the inside surface 55 of the activation ring 40 being non-circular in cross-section perpendicular to the axis 12 and with the corresponding outside surface of the housing being correspondingly non-circular.

A second optional rotational lock between the housing and the lock ring is provided in the above example by ribs 68 and arms 22, with ribs 68 extending either side of arms 22 in the circumferential direction. The rotational lock could also be provided in other ways, for example by the inside surface 55 of the lock ring 60 being non-circular in cross-section perpendicular to the axis 12 and with the corresponding outside surface of the housing being correspondingly non-circular.

The flexible arm 62 of the lock ring 60 is flexible in the circumferential direction is the example described above, but could alternatively flex in other directions such as the radial direction.

The support surface 66 is optional (the lock ring 60 does not have to abut the activation ring 40 for the mechanism to work, and in some embodiments a gap between the lock ring and the activation ring remains even after they are connected together), but could provide the limit to how far the needle shield can be pushed back. Alternatively, a limit can be provided elsewhere in the device, for example by limiting the distal movement of the needle shield by a protrusion on an outer housing.

The protrusion 70 is optional, and the distally-facing surface 72 on the lock ring could be provided on another part of the lock ring. The protrusion can interact with the arm of the housing to help keep the lock ring in place before use.

The spring 80 is optional. One alternative to having a spring is to have the needle shield attached to the activation ring as described below, in which case pulling the needle shield forwards would pull the activation ring forwards as well after use (the needle shield could be moved forwards by a needle shield spring, for example, or the user could pull the needle shield forwards manually by pulling the needle back in the proximal direction). The spring 80 extends between the housing and the activation ring in this example. In this example, the spring is inside the lock ring and is outside a tubular portion of the housing.

An autoinjector 100 is shown above as an example for context, but other designs of autoinjector or medicament delivery device more generally could also use the powerpack sub-assembly described herein. The activation mechanism described herein, where a second flexible arm 32 of the housing 20 is able to move away from the axis in the radial direction once the activation lock ring 60 has moved out of the way (e.g. FIG. 9), is optional, and other mechanisms of activation are also possible—for example by a button that can be operated by the user which is restricted from movement by the activation ring before the activation ring is moved in the distal direction, and which is able to move towards the axis in the radial direction after the activation ring is moved in the distal direction, thereby activating the device, for example by unlocking a plunger rod or activating a gas powered injection mechanism. Although not directly relevant to the lock concepts described herein, the powerpack sub-assembly also includes a power source. In some examples, the powerpack sub-assembly is gas-powered rather than mechanically powered as in the illustrated example (which is powered by a spring). The medicament delivery device may be a single-use product (disposable). Provision of a plunger rod is optional; in some examples, the stopper of the primary package can be moved in the proximal direction by another component or by an increase in pressure of the fluid adjacent to the stopper. Provision of a U-bracket is also optional. The U-bracket can provide one or more clicks, such as an end click, by being released and pushed against the housing 20 by the plunger rod spring 110. A guide rod 113 that extends inside the plunger rod spring 110 can be provided, as can be seen in FIG. 10, although this feature is also optional. The guide rod may be a part of the U-bracket (as shown in FIG. 10) or a separate component.

The examples above are described with a needle shield for context. This design can also be used with other medicament delivery members such as jet injectors, so the term 'needle shield' as used herein can be generalised to 'medicament delivery member shield'. Optionally, the activation ring 40 is an integral part of the needle shield 120. Optionally, the activation ring 40 is attached to the needle shield 120, for example by a snap fit or glue.

Various modifications to the embodiments described are possible and will occur to those skilled in the art without departing from the present disclosure which is defined by the following claims.

The invention claimed is:

1. A powerpack sub-assembly for a medicament delivery device, the powerpack sub-assembly extending along an axis in an axial direction from a proximal end to a distal end, the powerpack sub-assembly comprising a housing extending from the distal end of the powerpack sub-assembly, a lock ring slidable in the axial direction relative to the housing, an activation ring slidable in the axial direction relative to the housing and relative to the lock ring, wherein the lock ring is arranged closer to the distal end of the powerpack sub-assembly than the activation ring, a connection mechanism to connect the activation ring to the lock ring during use, the connection mechanism comprising a connector on the activation ring and a corresponding connector on the lock ring, and a lock mechanism to lock the powerpack sub-assembly after use, the lock mechanism comprising a distally-facing surface on the lock ring and a corresponding proximally-facing surface on the housing.

2. The powerpack sub-assembly of claim 1, comprising a spring arranged between the housing and the activation ring.

3. The powerpack sub-assembly of claim 1, the housing comprising a flexible arm extending in the proximal direction, wherein the proximally-facing surface on the housing is on the flexible arm.

4. The powerpack sub-assembly of claim 3, wherein the flexible arm is flexible in a radial direction relative to the axis.

5. The powerpack sub-assembly of claim 1, wherein the housing, the activation ring and the lock ring are all coaxial.

6. The powerpack sub-assembly of claim 1, wherein the housing comprises a tubular portion, and wherein the activation ring and the lock ring both extend around the tubular portion of the housing.

7. The powerpack sub-assembly of claim 1, wherein the connection mechanism is a snap-fit.

8. The powerpack sub-assembly of claim 1, wherein the connector on the lock ring is a hook on a flexible arm, and the connector on the activation ring is a protrusion or rib.

9. The powerpack sub-assembly of claim 8, wherein the flexible arm is flexible in a circumferential direction relative to the axis.

10. The powerpack sub-assembly of claim 1, wherein the housing and the lock ring are rotationally locked relative to one another, and wherein the housing and the activation ring are rotationally locked relative to one another.

11. The powerpack sub-assembly of claim 1, wherein during use, the activation ring is moveable in a distal direction from a position spaced apart from the lock ring to a position adjacent to the lock ring, and the activation ring and the lock ring are subsequently moveable together relative to the housing from a distal position to a proximal position, so as to lock the powerpack sub-assembly after use.

12. The powerpack sub-assembly of claim 1, wherein the connection mechanism connects the activation ring to the lock ring when the activation ring moves to the position adjacent to the lock ring.

13. The powerpack sub-assembly of claim 1, wherein the powerpack sub-assembly comprises a plunger rod and the housing comprises a flexible arm, wherein at least part of the flexible arm is inside the activation ring, and wherein a portion of the flexible arm of the housing extends into a recess in the plunger rod.

14. An autoinjector comprising the powerpack sub-assembly of claim 1.

15. The autoinjector of claim 14, wherein the autoinjector comprises a needle shield that abuts the activation ring.

16. A powerpack sub-assembly for a medicament delivery device, the powerpack sub-assembly extending along an axis in an axial direction from a proximal end to a distal end, the powerpack sub-assembly comprising:

a housing extending from the distal end of the powerpack sub-assembly;

a flexible arm connected to the housing and extending proximally;

a lock ring slidable in the axial direction relative to the housing;

an activation ring slidable in the axial direction relative to the housing and relative to the lock ring, where the lock ring is arranged closer to the distal end of the powerpack sub-assembly than the activation ring;

a connection mechanism to connect the activation ring to the lock ring during use, the connection mechanism comprising a connector on the activation ring and a corresponding connector on the lock ring;

a spring engaged with a distal end of the activation ring such that the spring biases the activation ring in a proximal direction; and a lock mechanism that locks the powerpack sub-assembly after use, where the lock mechanism comprising a distally-facing surface on the lock ring that engages a corresponding proximally-facing surface on a proximal end of the flexible arm.

17. The powerpack sub-assembly of claim 16, wherein the activation ring and the lock ring are both tubular and extend around a tubular portion of the housing.

18. The powerpack sub-assembly of claim 16, wherein the connection mechanism comprises an irreversible snap fit connector.

19. The powerpack sub-assembly of claim 16, wherein the lock ring and the activation ring are each rotationally locked relative to the housing.

20. The powerpack sub-assembly of claim 19, wherein the activation ring moves in a distal direction from a position spaced apart from the lock ring to a position adjacent to the lock ring causing the lock mechanism to engage to lock the lock ring and activation ring together such that the activation ring and the lock ring move together relative to the housing from a distal position to a proximal position to lock the powerpack sub-assembly after use.

* * * * *